United States Patent [19]
Lang

[11] Patent Number: 5,445,604
[45] Date of Patent: Aug. 29, 1995

[54] WOUND DRESSING WITH CONFORMABLE ELASTOMERIC WOUND CONTACT LAYER

[75] Inventor: Stephen M. Lang, Near Saffron Walden, United Kingdom

[73] Assignee: Smith & Nephew Associated Companies, Ltd., United Kingdom

[21] Appl. No.: 138,610

[22] Filed: Oct. 15, 1993

Related U.S. Application Data

[63] Continuation of Ser. No. 998,635, Dec. 31, 1992, abandoned, which is a continuation of Ser. No. 882,356, May 7, 1992, abandoned, which is a continuation of Ser. No. 432,808, Oct. 18, 1989, abandoned, which is a continuation of Ser. No. 791,720, Oct. 25, 1985, abandoned, which is a continuation of Ser. No. 345,488, Feb. 3, 1992, abandoned.

[30] Foreign Application Priority Data

May 22, 1980 [GB] United Kingdom ............... 8115742
Feb. 13, 1981 [GB] United Kingdom ............... 8104568

[51] Int. Cl.⁶ ............................................. A61F 13/00
[52] U.S. Cl. .................................... 602/47; 604/304; 604/307
[58] Field of Search ............... 604/304, 307, 369, 389, 604/390.1, 396, 397; 424/443, 445, 447, 448; 602/47

[56] References Cited

U.S. PATENT DOCUMENTS

| | | | |
|---|---|---|---|
| 2,896,618 | 7/1959 | Schaefer | 128/156 |
| 3,645,835 | 2/1972 | Hodgson | 428/195 |
| 3,678,933 | 7/1972 | Moore et al. | 128/156 |
| 3,709,221 | 1/1973 | Riely | 128/156 |
| 3,972,328 | 8/1976 | Chen | 128/156 |
| 4,753,231 | 6/1988 | Lang et al. | 128/156 |
| 4,860,737 | 8/1989 | Lang et al. | 602/47 |
| 5,147,338 | 9/1992 | Lang et al. | 602/47 |

*Primary Examiner*—Paul Prebilic
*Attorney, Agent, or Firm*—Rosenman & Colin

[57] ABSTRACT

Low adherency wound dressings which comprise a wound facing layer, an intermediate absorbent layer and an outer layer characterized in that the wound facing layer comprises a conformable elastomeric apertured film, the intermediate absorbent layer comprises a conformable hydrophilic foam and the outer layer comprises a continuous moisture vapor transmitting conformable film; materials therefor and processes for the manufacture thereof are described.

12 Claims, 2 Drawing Sheets

WOUND DRESSING WITH CONFORMABLE ELASTOMERIC WOUND CONTACT LAYER

The application is a continuation of 07/998,635 filed Dec. 31, 1992 (now abandoned) which is a continuation of 07/882,356 filed May 7, 1992 (now abandoned) which is a continuation of 07/432,808 Oct. 18, 1989 (now abandoned) which is a continuation of 06/791,720 Oct. 25, 1985 (now abandoned) which is a continuation of 06/345,488 Feb. 3, 1982 (now abandoned).

The present invention relates to an absorptive wound dressing suitable for use on burns or other wounds which dressing has a reduced tendency to adhere to the wound and can act as a bacterial barrier. The present invention also relates to the manufacture and use of such dressings.

Burns and other related wounds such as donor sites and the like present a serious problem in that they tend to produce large amounts of exudate which can cause conventional dressings to become saturated or to stick to the wound or even become infected. One method of covering such wounds has been to cover the wound with a material into which new epithelial or fibroblast growth can penetrate. Dressings of this kind are disclosed in U.S. Pat. Nos. 3,526,224, 3,648,692 and 3,949,742.

However such dressings can be-extremely painful to remove and often require surgical excision. A fundamentally different approach requiring a fundamentally different type of dressing is to employ materials that are designed to reduce the propensity to adhere to the wound. Dressings of this kind are disclosed in British Patent No. 439085, French Patent No. 947609, U.S. Pat. Nos. 3,543,750, 2,923,298 and British Patent No. 778813 which later patents cover successfully used materials such as Melolin ("Melolin" is a registered Trade Mark of T. J. Smith and Nephew Limited, Welwyn Garden City, Herts., U.K.). One more recent attempt at non-adherent dressings is U.S. Pat. No. 3,709,221 which discloses a dressing having an outer microporous, liquid repellent fibrous layer, an inner macroporous fibrous layer and an absorbent intermediate layer which was also envisaged as normally being fibrous. In order to reduce the tendency of this material to adhere to the wound the inner layer had to be treated with an agent to render it non-wetted by body liquid. It is now realised that it would be desirable to provide a dressing in which the wound facing layer did not require special treatment. As it will become apparent hereinafter it has now been discovered that by avoiding fibrous materials it is possible to produce a dressing with reduced tendency to adhere to wounds without the need for special treatments. An attempt at producing an absorbent dressing is described in U.S. Pat. No. 3,888,748 which describes a dressing fabricated from at least four sheet materials. The wound facing part of the dressing apparently consists of a grid or scrim coated with polyethylene in such manner that the polyethylene surrounds the filaments of the grid and collects any loose thread or particle that may be present in the core material. It is now realised that it is desirable to avoid the use of wound facing layers that can allow such penetration of the central layer to the wound surface. It has also been realised that it would be desirable to provide a material that was highly conformable to the wound so that it is possible to minimise the quantity of exudate between the wound surface and the dressing. U.S. Pat. Nos. 3,709,221 and 3,888,248 disclose materials which are bonded along their edges which may reflect a desire to improve conformability. The dressing of the present invention allows for bonding over the whole of the operative area while retaining flexibility.

Accordingly the present invention provides a low adherency wound dressing which comprises a wound facing layer, an intermediate absorbent layer and an outer layer which wound dressing is characterised in that the wound facing layer comprises a conformable elastomeric apertured film, the intermediate absorbent layer comprises a conformable hydrophilic foam and the outer layer comprises a continuous moisture vapour transmitting conformable film.

Normally the three layers of the dressing of this invention are attached in a contiguous and co-extensive manner; that is the dressing is normally provided in the form of a laminate.

The conformable elastomeric apertured film of the dressing of this invention acts as a low adherency wound facing layer. This layer allows wound exudate to pass to the absorbent layer but prevents the absorbent layer making direct contact with the wound surface.

Preferably the elastomeric apertured film is sufficiently conformable to allow the wound dressing to conform to the body contours and thereby maintain overall contact with the wound surface to ensure that exudate from the wound is absorbed.

It is also desirable that the elastomeric apertured film should be sufficiently elastically extensible to adjust to any dimensional changes in the absorbent layer which may occur, for example, expansion on liquid uptake.

Normally the elastomeric apertured film is made of a pharmaceutically acceptable water insoluble polymer. Preferred polymers for use are elastomers. Suitable elastomers include polyurethanes, polybutadiene and the like. The preferred materials for the apertured films are thermoplastic polyurethanes and polybutadienes.

Preferred thermoplastic polyurethanes are linear polyurethanes containing polyether or polyester groups-Suitable linear polyester polyurethanes are disclosed in U.S. Pat. No. 2,871,218. Suitable linear polyether polyurethanes are disclosed in U.S. Pat. No. 2,899,411. Favoured thermoplastic polyurethanes include Estanes from B. F. Goodrich Corp. Preferred solution casting grades are Estane 5714F1, 5702, and 5703. A preferred extrusion grade is Estane 580201.

Suitable polybutadienes are 1,2 polybutadienes. Favoured 1,2 polybutadienes contain a major amount of syndiotactic 1,2 polybutadiene, have a crystallinity of 25% to 30% and an average molecular weight in excess of 100,000. Preferred 1,2 polybutadienes are known as RB 810, RB820 and RB 830 made by Japan Synthetic Rubber Co.

The number and size of the apertures in the apertured film will be sufficient to allow the wound exudate to pass through the film to the absorbent layer. Most aptly the apertured film is adapted so that the size of apertures in combination with the thickness of the film prevent the absorbent layer contacting the wound surface. Suitable apertured films have apertures with a dimension of from 0.05 to 4 mm, more aptly from 0.05 to 2.5 or 0.05 to 2 mm and preferably from 0.1 to 2.5 mm. Suitable apertured films have a thickness of 0.01 to 2.5 mm, typically 0.01 to 0.25 mm and preferably of 0.05 to 0.5 mm.

Favoured apertured films of the invention have 4 to 40 apertures per cm with a dimension of 0.05 mm to 2.5 mm.

The conformable apertured film can be in any convenient form such as a perforated film or a net.

In a favoured aspect of the invention the elastomeric apertured film is in the form of a net which is preferably an integral net. The term 'intergral net' means a net in which the strands and junctures are formed integrally during manufacture.

The integral net of the wound dressing of the invention can have any convenient form depending on the chosen arrangement of strand, juncture and hole areas and also their shapes and relative size.

In one preferred form the net consists essentially of longitudinal and transverse strands intersecting at right angles to give a square grid hole pattern.

Suitable nets of this type aptly have 2 to 40 strands per cm desirably 4 to 40 strands per cm and preferably 2 to 24 strands per cm in both longitudinal and transverse directions.

Variations on the square grid pattern can give other desirable forms of the integral net. Unequal density of strands in either the longitudinal or transverse directions will give rectangular hole areas. Continuous parallel strands in one direction with a staggered arrangement of connecting strands in the other direction will give a "brickwork" pattern. Other apt forms of the integral polymer nets can have strands at an angle to the longitudinal or transverse direction (that is diagonal strands). Another preferred form of the integral polymer net can have a staggered arrangement of circular or approximately circular (for example hexagonal) arrangements of strands and hole areas. The integral polymer net can be in the form of a mixed pattern of two or more of the arrangements if desired.

The apertured film used in this invention aptly will have a weight of 10 gsm to 80 gsm and preferably will have a weight of 15 gsm to 50 gsm.

The desirable conformability of the wound dressing of the invention is consistent with the use of elastomeric materials such as integral nets of polyurethane or other elastomer.

Suitable integral nets of polyurethane or other elastomer will have an elongation at break of 100% to 800%, desirably of 200% to 750% and preferably of 300% to 700% when measured as a 2.5 cm wide strip at 30 cm/min strain rate at 20° C.

Other suitable conformable apertured films are thin flexible elastomeric films which have been perforated.

The continuous moisture vapour transmitting conformable film outer layer of the wound dressing of the invention may be used to regulate the moisture loss from the wound area under the dressing and also to act as a barrier to bacteria so that bacteria on the outside surface of the dressing cannot penetrate to the wound area.

Suitable continuous conformable films will have a moisture vapour transmission rate of 300 to 5000 grams preferably 500 to 2000 grams/square meter/24 hrs at at 37.5° C. at 100% to 10% relative humidity difference. It has been found that such moisture vapour transmission rates of the continuous film allow the wound under the dressing to heal under moist conditions without causing the skin surrounding the wound to macerate.

This outer layer will be made of polymer.

Suitable polymers for use in the outer layer include urethanes and copolymers of alkoxy alkyl acrylates or methacrylates such as those disclosed in British Patent No. 1,280,631.

Preferably the outer layer is a conformable polyurethane film.

Preferred polyurethane films are made from linear polyurethanes as hereinbefore described with respect to the wound facing layer. Favoured continuous films will be 12.5 micron to 37.5 micron thick. A preferred polyurethane for use in such thickness is Estane 5714F. A 25 micron thick film of Estane 5714F has a moisture vapour transmission rate of approximately 1800 g/m$^2$/24 hours/37.5° C. at 100% to 10% relative humidity difference so that it may be employed to produce a moisture vapour transmission within the preferred range.

The outer layer can be a conformable polyurethane-incompatible polymer blend film continuing voids.

Suitable conformable polyurethane blend films are disclosed in United Kingdom patent application No. 8122250.

Apt conformable polyurethane blend film outer layers have a thickness of 0.0125 m to 0.125 mm. Such films can have a moisture vapour transmission rate of at least 500 g and preferably at least 1000 g/m$^2$/24 hours/at 37.5° C. at 100% to 10% relative humidity difference.

A preferred polyurethane blend film comprises a blend of a linear polyurethane (60 parts by weight of Estane 580201 available from B. F. Goodrich) and a high impact polystyrene (40 parts by weight of compound ref. 6 mw available from R. H. Cole Limited). A favoured film of this composition has a thickness of 0.084 mm and a moisture vapour transmission rate of 1660 g/m$^2$/24 hours/at 37.5° C. at a 100% to 10% relative humidity difference.

The continuous moisture vapour transmitting conformable film outer layer can comprise a moisture vapour transmitting adhesive layer.

In such adhesive containing outer layers the adhesive layer will be covered by an extensible moisture vapour transmitting layer to provide a non adhesive surface on the outer layer of the dressing.

At least one of the adhesive or extensible layers will be continuous.

Preferred adhesive layers are continuous. Suitable adhesives which are moisture vapour transmitting as a continuous layer include various acrylate ester copolymers, polyvinyl ethyl ether and polyurethane pressure sensitive adhesives. Examples of suitable pressure sensitive adhesives are given in British Patent No. 1,280,631.

A preferred pressure sensitive adhesive comprises a blend of a high and low viscosity polyvinyl ethyl ethers in particular 'adhesive composition A' disclosed in British Patent Specification No. 1,280,631. Other preferred pressure sensitive adhesives comprise copolymers of acrylate ester with acrylic acid for example as disclosed in United Kingdom Application No. 8106707 and in particular a copolymer of 47 parts by weight of butylacrylate, 47 parts by weight of 2 ethyl hexyl acrylate and 6 parts by weight of acrylic acid with an intrinsic viscosity of at least 1.9 dl/g polymerised in acetone according to the general method given in above United Kingdom application.

The suitable continuous adhesive layers can have a weight per square meter of 15 g to 70 g and preferably of 20 g to 40 g.

The extensible moisture vapour transmitting layer which covers the adhesive layer can be the comformable continuous films hereinbefore described. Alternatively the extensible layer can be a discontinuous layer.

Suitable discontinuous extensible layers include apertured non woven fabrics which are extensible in at least one direction.

Preferred extensible apertured non woven fabrics include those made from bonded viscose filaments. Suitable fabrics of this kind are available as Bemliese (Trade Mark) from Asahai Chemical Company. Bemliese is available in weights per square meter ranging from 18 g to 45 g. A favoured fabric is Bemliese G204 which has a weight per square meter of 18.5 g.

The conformable hydrophilic polymer foam absorbent layer used in the dressing of this invention is adapted to be capable of absorbing the wound exudate e.g. from a burn. It is desirable that the hydrophilic foam layer absorbs the wound exudate rapidly as this enhances the low adherency properties of the dressing. Such rapid absorption prevents pooling of exudate between the dressing and the wound and it has been found that this prevention of pooling is desirable.

Suitable conformable hydrophilic foams will normally be flexible, open cell foams.

The ability of open cell foams to absorb and retain fluids depends to some extent on the size of foam cells and the porosity of the foam.

Suitable open cell hydrophilic foams of dressings of the invention have a cell size of of 30 microns to 700 microns and preferably a cell size of 50 microns to 500 microns. Apt open cell hydrophilic foams of dressings of the invention have 20% to 70% and preferably 30% to 60% of the total membrane area of the cells as membrane openings. Such open cell foams permit transport of fluid and cellular debris into and within the foam.

Apt foams may be polyurethane, carboxylated butadiene styrene rubber, polyacrylate or the like foam. Such foams may be made of hydrophilic materials per se or may be treated to render them hydrophilic, for example with surfactants. It is much preferred to use foams which are made of polymer which is itself hydrophilic as it has been found that the exudate is less likely to coagulate rapidly. The use of such foams of hydrophilic polymer in dressings of the invention can allow the wound to be maintained in a moist condition even when the exudate produced has been absorbed and removed from the wound surface.

Favoured hydrophilic polymer foams are hydrophilic polyurethane and especially those which are made of crosslinked hydrophilic polyurethane. Preferred foams can be made by reacting a hydrophilic isocyanate terminated polyether prepolymer with water. Favoured hydrophilic polyurethane foams of this type include those known as Hypol foams. Hypol foams can be made from Hypol hydrophilic prepolymers marketed by W. R. Grace and Co.

Suitable hydrophilic foam absorbent layers have a thickness of 0.5 mm to 20 mm, more suitably 0.8 mm to 15 mm and preferably 1 mm to 12 mm.

The wound dressings of the invention preferably consist of a conformable elastomeric apertured film, an intermediate conformable hydrophilic polymer foam layer and a continuous moisture vapour transmitting conformable polymer film outer layer in which the layers are attached in a contiguous and co-extensive relationship.

The wound dressing of this invention may be in any convenient form. A preferred form is a pad of rectangular shape. Suitable sizes of such a pad are from 10 cm to 20 cm×30 cm. Another preferred form is an elongate strip which may be in the form of a roll. Such a strip may be used as a bandage or may be used to prepare smaller dressings.

It is desirable that the wound dressing of this invention are sterile. The wound dressing of the invention is advantageously provided in bacteria impervious pouches. Such packed forms can be prepared under aseptic conditions or alternatively sterilised after packing by a conventional procedure. A favoured sterilisation procedure is heat sterilisation, for example by steam. Another favoured procedure is ethylene oxide sterilisation or gamma irradiation.

In another aspect the invention provides a process of making a low adherency wound dressing which comprises bringing together of a conformable elastomeric apertured film layer, an intermediate absorbent layer comprising a conformable hydrophilic polymer foam and an outer layer comprising a continuous moisture vapour transmitting conformable film.

Normally the bringing together of the layers will be a lamination process.

The previously formed individual layers can be formed into a laminate by bonding the layers together in one or more laminating processes. Suitable bonding methods include heat sealing or adhesive bonding providing the adhesive layer is moisture vapour transmitting.

In a preferred process the foam layer is formed in contact with one or both of the other layers. This process is favoured as it reduces or eliminates the number of special bonding operations.

In another preferred process the outer conformable film layer is formed on the foam layer for example by spraying a solution of the polymer.

In a continuous process the wound dressing can be made in the form of a continuous strip which is then cut up into suitable sized dressings.

The conformable hydrophilic polyurethane foam can be made by mixing together an isocyanate terminated polyether having functionality of more than two with a surfactant and water and casting the mixture onto a surface. This surface advantageously may be the outer film of the dressing or the wound facing layer of the dressing. Preferred isocyanate terminated polyethers include Hypols FHP 2000, 2001, 3000, 3001, 2002 and 2000HD marketed by W. R. Grace & Co. Hypols are described in a booklet published by W. R. Grace and Co. "Hypol: foamable hydrophilic polymers-laboratory procedures and foam formulation". Their preparation and use are disclosed in British Patent Specifications No. 1,429,711 and 1,507,232.

Suitable surfactants for forming conformable hydrophilic polymer foams include non-ionic surfactants. Favoured non-ionic surfactants are oxypropylene-oxyethylene block copolymers known as Pluronics marketed by BASF Wyandotte. Preferred Pluronics include L64, F87, P38, P75 and L62. Another favoured non-ionic surfactant is a polyoxyethylene stearyl ether known as Brij 72 marketed by Honeywell Atlas.

To prepare a suitable foam 100 parts by weight of Hypol FHP 2000, 2001, 3000, 3001, 2002 or 2000HD is mixed with 0.3 to 7 parts by weight of surfactant-or mixtures of surfactants and 30 to 300 parts by weight of water and the foaming mixture cast onto a surface. Typical foaming mixtures have a cream time of about 20 secs., a rise time of about 250 secs. and a cure time of about 400 secs.

In a continuous process for forming the foam the ingredients are fed into a continuous mixing and dispensing machine. Suitable conformable hydrophilic polymer foam layers can be made by Casting the foaming mixture before it sets onto a suitable surface by means of a casting head.

A suitable mixing and dispensing machine is known as Vario-mix supplied by Prodef Engineering Limited. The foam mix can conveniently be delivered to the casting head by means of a 'fish tail' die.

In a preferred process of forming the dressing in which the foam layer is produced in contact with an external layer it is important that the other external layer should be laminated to the expanded foam while the foam is still tacky so as to obtain a good bond. Typically 2.5 minutes to 5 minutes, for example 3 mins to 3.5 mins, after the foam has been cast is suitable for bringing the foam into contact with the other external layer.

Figure 1:
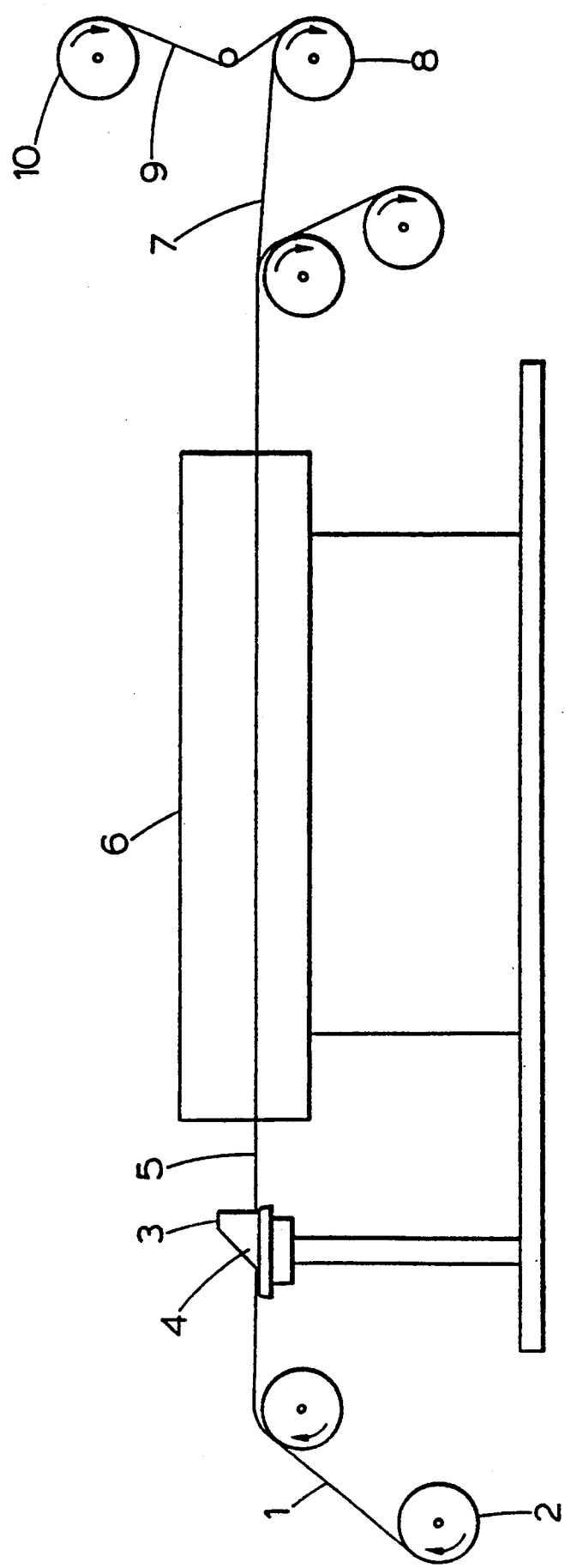
FIG. 1 illustrates a process of making the conformable integral polymer nets of the wound dressing of the invention.

In FIG. 1 a thermoplastic film (1) with an embossed pattern on its upper surface may be fed from roll (2) to the coating head (3) where a solution (4) may be cast into the recesses of the embossed sheet. The wet cast net (5) on the embossed sheet may be passed into an oven (6) where it is dried. The dried cast net (7) may then be separated from the embossed sheet (1) and wound up onto roller (8) where it may also be interleaved with a release paper (9) fed from the roll (10).

In an alternative and preferred process the dried cast net is left on the embossed sheet.

The coating head (not shown) has an adjustable doctor blade supported on a flat bed to meter the casting solution and side guides to regulate the width of the cast net. It is preferred that the doctor blade has a base portion which is thick enough to span the discrete raised areas of the embossed film to prevent the doctor blade catching in the recessed areas of the film. The doctor blade and the guides can be coated or made of a fluorocarbon polymer for example polytetrafluoroethylene to reduce friction against the film. Alternative coating heads using fixed or rotating rollers can also be used.

A favoured coating head comprises an adjustable doctor blade which is supported on a soft base, for example a base consisting of a movable rubber belt around two rotatable rollers, to meter the casting solution.

Figure 2:
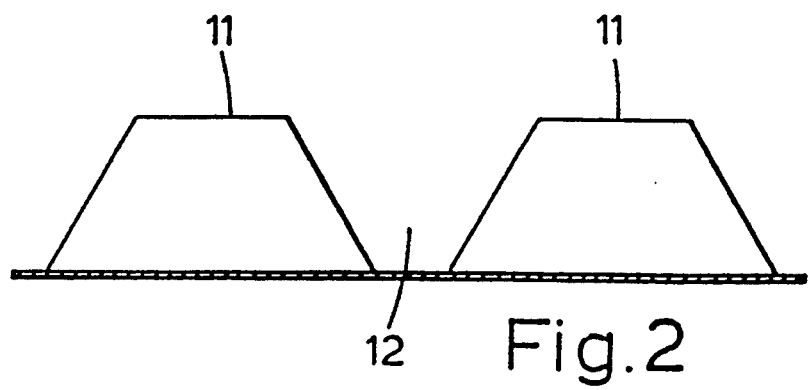
FIG. 2 is a plan view of an embossed pattern sheet casting surface for forming an integral polymer net.

FIG. 2 shows discrete raised areas (11) arranged in a square pattern to give a square grid pattern of recesses (12) on the embossed casting sheet.

Figure 3:
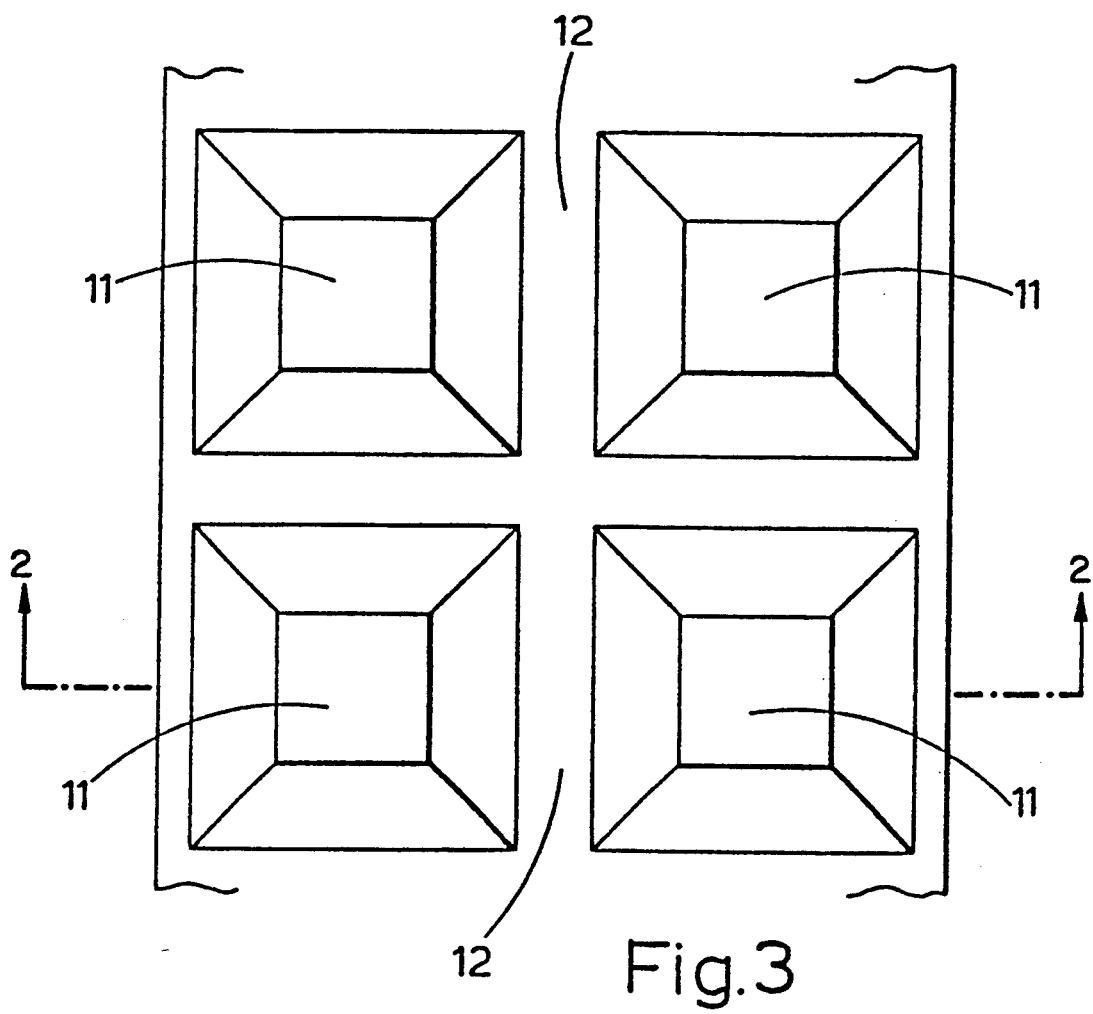
FIG. 3 is a cross-section through line A—A of FIG. 2.

In FIG. 3 a section through line A—A of FIG. 2 shows the discrete raised areas (11) in the shape of truncated square pyramids and recesses (12).

The integral nets of polyurethane can be made by casting the polyurethane in a flowable state onto a surface having a pattern of discrete raised areas and interconnected recessed areas and treating the cast net to form a solid integral net. The flowable state of the polyurethane can include solutions, dispersions, hot melts and powders which can be dried, coated, fused or otherwise to form a solid net. The casting surface may be in the form of a roller, an endless flexible belt or a length of sheet material. It is preferred that the casting surface has release properties to enable the formed net to be removed from the casting surface. The pattern of the discrete raised areas and interconnected recessed areas on the casting surface selected dictates the structure of the resulting net.

A preferred method of making the integral nets of polyurethane is by casting a solution of a thermoplastic polyurethane onto a melt embossed polyolefin sheet and drying the cast net in a hot oven.

Suitable casting solutions can contain 15% to 35% by weight of thermoplastic polyurethane, preferably 20% to 30% by weight. Favoured casting solutions contain 20 to 25% by weight of Estane 5702 or Estane 5703 in acetone. Another favoured solution contains 25% to 30% by weight of Estane 5714F in tetrahydrofuran or mixtures of tetrahydrofuran and acetone.

Analogous procedures may be used to prepare nets from other elastomers.

The melt embossed polyolefin sheet can be made by the method given in British Patent Specification No. 1,055,963 A suitable embossed polyolefin sheet has a pattern of 8 per cm raised areas in the form of square truncated pyramids 1 mm. wide and 0.5 mm high with side sloping to a 60° C. conical angle and longitudinal and transverse square grid recesses 0.25 mm wide at the base and 0.75 mm at the top.

A favoured embossed polyolefin sheet has a pattern of 6 per cm raised areas in diagonal rows (45°) of square truncated pyramids 1.35 mm wide at their base, 0.7 mm wide at their top and 0.45 mm high with sides sloping to a 70° conical angle.

A preferred embossed polyolefin sheet has a pattern of 4 per cm raised areas in diagonal rows (45°) of square truncated pyramids 2 mm wide at their base, 1.425 mm wide at their top and 0.5 mm high with sides sloping to a 60° to a conical angle.

The solution of thermoplastic polyurethane can be cast onto the embossed polyolefin surface by means of a casting head consisting of a knife over a flat bed, or knife over a roller or knife over soft bed.

Suitable conformable polyurethane films for the outer layer of the dressing can be formed by casting or spraying from solution, hot melt coating or film extrusion in a conventional manner.

Preformed polyurethane films can be formed on a release surface for example a silicone release coated paper.

Suitable casting solutions are described hereinbefore in relation to making integral polyurethane nets wound facing layers.

In an alternative process the conformable polyurethane film can be formed on the conformable hydrophilic foam layer. In an apt process the polyurethane solution is sprayed onto the foam layer. The spraying of the polyurethane solution can be carried in a conventional manner for example using an air spray gun. A suitable spray gun is model 630 available from Binks Bullow Limited.

Suitable methods of making voided polyurethane-incompatible blend film outer layers are disclosed in United Kingdom Application No. 8124250.

The adhesive layer of the outer layer can be formed by any convenient method including solution and emulsion coating, coating from a hot melt and by extrusion. The adhesive layer can be coated directly onto a substrate of the dressing for example the extensible apertured non woven fabric layer. However, it is preferred that the adhesive layer is coated onto a release surface and the dried adhesive transferred by lamination onto the desired substrate.

The wound dressing of the invention can contain topically effective medicament. Most suitably the medicament is an antibacterial agent. Preferably the antibacterial agent is a broad Spectrum antibacterial agent such as a silver salt such as silver sulphadiazine, an acceptable iodine source such as povidone iodine (also called polyvinyl pyrrolidone iodine or PVP/I), chlorhexidine salts such as the gluconate, acetate, hydrochloride or the like salts or quaternary antibacterial agents such as benzalkonium chloride or the like.

A preferred medicament for inclusion in the dressing of this invention is silver sulphadiazine. A further preferred medicament for inclusion in the dressing of this invention is chlorhexidine which will normally be present as one of its aforementioned salts, The medicament may be present by 0.2% to 20%, more usually from 0.3 to 10% and preferably 0.5 to 5% by weight of the dressing, for example 1%, 1.2% or 3% and the like. The medicament is present in the invention in the foam layer.

It is one of the surprising features of this invention that antibacterial agents can be incorporated into a hydrophilic polyurethane foam and will thereafter be available to aid in maintaining the wound to which the dressing is applied free of infection.

It is particularly surprising that medicaments such as silver sulphadiazine and chlorhexidine hydrochloride and the like can be incorporated into the proto foam prior to Polymerisation since the presence of compounds containing basic nitrogen atoms may well have been expected to radically change the nature of the foam which has now been found not to occur.

The medicament may be introduced into the foam either by incorporation prior to foaming or by incorporation into the intact foam which has previously been prepared.

If the medicament is to be introduced prior to foaming then the medicament must either be free of reactive moieties which would react with the components of the mixture to be foamed (for example it must not contain free amino groups which could react with the isocyanates present) or else the medicament must be of low solubility so that its potential reactivity is suppressed. Thus for example medicaments such as silver sulphadiazine and chlorhexidine hydrochloride are easily incorporated into the foam by dispersing the desired amount of the meidcament into the prepolymer mixture, for example dispersing it within the aqueous solution of the surfactant before mixing with the isocyanate containing materials. Most suitably the insoluble medicaments are in finely divided form and are most preferably micronised.

It has been found that more soluble salts such as chlorhexidine gluconate cannot be incorporated in this fashion since reaction with prepolymer components can occur and a more rigid and antibacterially ineffective foam results. Fortunately it has now been discovered that soluble medicaments can be included into the foam after it has been prepared by soaking the foam in a solution of the medicament. Thus for example a 2×2 cm dressing of this invention suspended in 50 mls of 5% w/v solution of chlorhexidine gluconate for 48 hours and dried was found to posess antibacterial properties.

In a favoured embodiment of the invention the wound dressing may be in the form of a compression bandage.

Most aptly the compression bandage of this invention has more than one elastic layer. In another aspect this invention provides a low adherency compression bandage which comprises a wound facing layer of elastomeric apertured film, an intermediate layer of a conformable hydrophilic foam and an outer layer of an elastomeric continuous moisture vapour permeable film.

Most aptly the elastomeric apertured film is a net as hereinbefore described.

In preferred compression bandages of this invention the integral net wound facing layer, the intermediate foam layer and the outer film layer are made of polyurethane as hereinbefore described.

Low adherency compression bandages of the invention can be used to cover skin grafts. In this application the bandage may absorb exudate from the graft surrounds and at the same time exert an even pressure over the graft site which can protect against hypertrophic scarring.

The low adherency compression bandages of this invention may also be used in the treatment of ulcers, for example leg ulcers.

The bandages of this invention will normally be presented as rolls of from 1 to 4 meters length and 5 to 20 cms width.

After fabrication the wound dressing of this invention can be washed with water to remove excess surfactant and then dried.

Surprisingly the method of drying has been found to greatly affect the appearance of the dressing.

Some air dried dressings have been found to curl. In some cases the outer film has puckered thereby giving the film a grained appearance and texture of skin.

Dressings autoclaved using vacuum drying cycle have been found to tend to remain flat. The outer film layer has a puckered surface. Partially dried dressings, that is dressings containing low levels of residual water absorbed into the foam polymer but not into foam air spaced have been discovered to be flat. This unanticipated effect is rendered even more useful since the dressing will remain flat if protected against loss of water, for example if packaged in a water proof pouch such as an aluminium foil pouch. In such partially dried dressings the film and net are not puckered.

Dressings containing residual amounts of water in this way have been found to have a pleasant cooling feel.

As previously indicated hereinbefore the dressings of this invention may be adapted to release an antibacterially effective amount of an anti-bacterial agent into the wound covered by the dressing. Thus in an alternative aspect this invention provides a method of treating a wound so as to aid in rendering or maintaining it free of infection which comprises contacting the wound with a dressing of this invention adapted to release an antibacterial agent. Most aptly this aspect of the invention is employed in rendering or maintaining burns free of infection. The antibacterial agent present is favourably a silver salt such as silver sulphadiazine or a chlorhexidine salt such as chlorhexidine hydrochloride or a mixture thereof. Preferably the antibacterial agent present is silver sulphadiazine.

The absence of fibres in the dressing enhances the non adherent properties of the wound dressings of the invention.

Description

Preparation of Integral Polyurethane Net

A solution containing 30% by weight of Estane 5714F1 in tetrahydrofuran was cast into the recesses of a 15 cm wide melt embossed high density polyethylene sheet by means of the blade over flat bed spreading technique. The sheet had a melt embossed pattern of 8 per cm raised areas in the form of square truncated pyramids 1mm wide at their base and 0.5 mm high with sides sloping to a solid conical angle of 60° C. The wet cast net on the embossed film was dried by passage through a hot air circulating oven at a temperature of 90° C. to 100° C. for two minutes. The dried cast net was separated from the embossed film and wound onto a roller interleaved with a double sided silicone release paper.

The resultant cast integral of elastomeric polyurethane net had the following properties: Weight 40 gsm; thickness 100–125 microns; aperture size 0.3 to 0.4 mm; tensile strength (g/2.5 cm wide), machine direction 800±51, transverse direction 664±57, elongation at break %, machine direction 389±24, transverse direction 374±24.

Preparation of Integral Polyurethane Diamond Pattern Net (6 apertures/cm).

The net was cast in the same manner as the preceeding square net except that the casting sheet had a melt embossed pattern of 6 per cm raised areas in diagonal rows (45°) of square truncated pyramids 1.35 mm wide at their base and 0.45 mm high with sides sloping to a conical angle of 70°

Example 1

Preparation of a low adherency wound dressing

A mixture of Brij 72 (22.5 g of 2% aqueous emulsion) and Pluronic F87 (0.5 ml of a 10% aqueous solution) was added to Hypol FHP3001 (15 g) in a beaker and thoroughly mixed by stirring with a metal spatula until the Hypol was uniformly dispersed (20 seconds). The foaming mixture was poured into a 15 cm wide brass hand spreader box set at a gap of 1.8 mm above a 25 micron thick cast Estane 5714F1 film. The spreader box was then drawn by hand along the film surface to leave a foam layer on the film The cast integral polyurethnae net of the description was then laminated to the foam by placing the net (smooth surface uppermost) onto the setting foam 3 minutes to 3.25 minutes after the spreading had commenced. The foam layer was free of large craters and was well bonded to the net.

Alternatively the wound dressing can be made in a similar manner by coating the loam onto the integral polyurethane net (preferably on the embossed film carrier) and laminating the film to the setting foam.

Sample wound dressings of Example 1 and the comparison hydrophilic polyurethane foam were washed with distilled water and dried at 40° C. for 12 hours before being tested for wound adherency.

Example 2

Brij 72 (30 g as a 2.5% aqueous solution) was added to Hypol FHP 3001 (20 g) in a beaker and mixed by stirring with a metal spatula and then with a mechanical stirrer until the Hypol was uniformly dispersed (approximately 20 seconds). The foaming mixture was cast onto a 6 aperture/era diamond pattern net as described above on its embossed film carrier by means of a blade over flat bed coating head set at a gap of 0.1 mm. A 25 micron thick film (Estane 5714F1) on a silicone release paper was laminated to the foam surface with light manual pressure to the foam surface while it was still tacky (approximately 3 minutes after spreading). After 15 minutes the embossed film and silicone coated release papers were removed from the net and film surfaces of the strip and the strip cut into 30 cm×15 cm wound dressings. The dressings were washed in two changes of 1 liter of distilled water and dried in air.

Example 3

Wound dressings were prepared in the same manner as Example 2 using a gap setting of 0.5 mm instead of 0.1 mm.

Example 4

Wound dressings were prepared in the same manner as Example 2 using a gap setting of 1.0 mm instead of 0.1 mm.

Example 5

The wound dressings of Example 3 were autoclaved at 116° C. for 30 minutes followed by a vacuum drying cycle.

Example 6

The wound dressings of Example 4 were autoclaved in the same manner as Example 5.

Example 7

The dressings of Example 4 were washed but only partially dried by padding with an absorbent towel.

The following Examples 8 to 12 the preparation of of medicated wound dressings of the invention.

Example 8

Wound dressings were prepared in the same manner as Example 3 except that silver sulphadiazine powder (0.2 g) was blended into the Brij 72 emulsion with a high speed shear mixer prior to the addition of Hypol FHP 3001.

Example 9

Wound dressings were prepared in the same manner as Example 8 using 1 g of chlorhexidine hydrochloride powder instead of silver sulphadiazine powder (0.2 g).

Example 10

Wound dressings prepared as in Example 3 were soaked for 10 minutes in a tray containing an aqueous solution of chlorhexidine gluconate (5% weight/volume) and air dried.

Example 11

Wound dressings were prepared in the same manner as Example 10 using an aqueous solution of chlorhexidine acetate (5% weight/volume) instead of an aqueous solution of chlorhexidine gluconate.

Example 12

Wound dressings were prepared in the same manner as Example 10 using an aqueous solution of povidone iodine (10% weight/volume) instead of an aqueous solution of chlorhexidine gluconate.

Example 13

Wound dressings were prepared in the same manner as Example 7 using 20 g instead of 30 g of Brij 72.

Example 14

Wound dressings were prepared in the same manner as Example 7 using 40 g instead of 30 g of Brij 72.

Example 15

Wound dressings were prepared in the same manner as Example 7 with 0.5 ml of Pluronic L64 (10% aqueous solution) added to the surfactant emulsion.

Example 16

Wound dressings were prepared in the same manner as Example 15 using Pluronic F68 in place of Pluronic L64.

Example 17

Wound dressings were prepared in the same manner as Example 15 using Pluronic F108 instead of Pluronic L64.

Example 18

Wound dressings were prepared in the same manner as

Example 1 using Brij 72 (30 g as a 2.5% aqueous emulsion) instead of a mixture of Brij 72 (22.5 g as a 2% aqueous emulsion) and Pluronic F87 as a 10% aqueous solution).

Example 19

Wound dressings were prepared as Example 18 using a mixture of Brij 72 and a Pluronic P75 (0.5 ml as a 10% aqueous solution).

Example 20

Wound dressings were prepared in the same manner as Example 1 using a cast polybutadiene (ref RB830) net (8 apertures per cm) instead of a polyurethane net.

Example 21

Preparation of a Compression Bandage

A bandage strip was made in the same manner as the wound dressing strip of Example 2 using a blade gap setting of 0.5 mm. The strip was washed in distilled water and dried in air. A 1 cm wide bandage had the following stress-strain properties:

| Strain % | Stress g/cm |
|---|---|
| 25 | 360 |
| 50 | 610 |
| 100 | 800 |

To illustrate the compression properties of the bandage the pressure (P) exerted on a-limb of radius (R) by a single layer of the bandage stretched by different amounts was calculated from the stress-strain properties above using the equation $p=F/R$ where F is the force (g/cm) to stretch the bandage by a given amount.

| | stretched length (% of original length) | $g/cm^{-2}$ | $P_{mmHg}$ |
|---|---|---|---|
| Arm 10 cm in | 125 | 72 | 54 |
| diameter | 150 | 122 | 92 |
| | 200 | 160 | 120 |
| Leg 20 cm in | 125 | 36 | 27 |
| diameter | 150 | 61 | 46 |
| | 200 | 80 | 60 |

Antibacterial properties of the Medicated Dressings 15 mm diameter samples of medicated wound dressings of Examples 9 to 14 were moistened and placed on agar plates seeded with *staphyloccocus aureus* or *bacillus subtilis* and incubated for 24 hours at optimum temperature for growth. The zones of inhibition produced by diffusion of the medicament from the dressings were measured.

| | | | Zone diameter | |
|---|---|---|---|---|
| Example | Medicament | | *Staph aureus* | *B. subtilis* |
| 8 | silver sulphadiazine | | 30 | 29.5 |
| 9 | chlorhexidine Hcl | | 23.8 | 21.6 |
| 12 | povidone iodine | | 29.6 | 19.4 |
| 11 | chlorhexidine acetate | | 29.0 | 32.0 |
| 10* | chlorhexidine gluconate | (1) | 22.6 | 23.5 |
| | | (2) | 19.8 | 19.1 |
| | | (3) | 16.8 | 16.0 |
| control | (no medicament) | | 0 | 0 |

*consecutive tests on the same sample to measure the effect of the sustained release of the medicament from the dressing.

Example 22

Preparation of Integral Diamond Pattern Net (4 apertures/cm)

A solution containing 20% by weight of Estane 5714F in 60/40 (weight by weight) mixture of Tetrahydrofuran acetone was cast into the recesses of a 15 cm wide melt embossed high density polyethylene sheet by means of a blade over soft bed coating technique. The sheet had a melt embossed pattern of 4 per cm raised areas in diagonal rows (45°) of square truncated pyramids 2 mm wide at their base, 1.42 mm wide at top and 0.5 mm high with sides sloping to a conical angle of 60° The wet cast net in the embossed film was dried by passage through a hot air oven at temperature of 80° C. for two minutes.

The net had a weight per square meter of 33 g and had 4 per cm apertures of approximately 1.4 mm in size.

Preparation of the absorbent layer

Using a two component dispensing unit (Vario-mix supplied by Prodef Engineering Limited), a foaming mixture was formed by mixing Hypol FHP 2002 and Brij 72 (2% aqueous solution) in the ratio of 1:2.25. The foaming mixture was fed into the coating head by means of an output nozzle in the form of a 15 cm 'fish tail die' and coated onto the cast polyurethane net (on embossed film) by means of a knife over roller coating head set at a gap of 1 min. The cast foam was dried by passage through an air circulating oven at a temperature of 50° C. for 5 minutes.

Preparation of the Conformable Film Outer Layer

A solution containing 2% by weight a polyurethane of (Estane 5714F) in a 60/40 (weight by weight) mixture of tetrahydrofuran/acetone was hand sprayed onto the foam surface of the composite foam/net strip using an air spray unit (model 630 supplied by Binks Bullow Limited) and dried by passage through an air circulating oven heated to a temperature of 70° C.

The polyurethane coating was found to be continuous and had a weight per square meter of approximately 30 grams.

The embossed film was then removed from the three layer composite strip and the strip cut into dressings of suitable size for adherency testing.

Example 23

A foam-net composite strip on embossed film was made in the same manner as example 22.

An extensible apertured non woven fabric (Bemliese GS 204) coated with a continuous layer of a moisture vapour transmitting acrylate copolymer adhesive (30 g/m$^2$) was laminated to the foam side of the composite strip to form a conformable outer layer.

The adhesive was a copolymer of 47 parts by weight n-butyl acrylate, 47 parts by weight of 2-ethyl-hexyl acrylate and 6 parts by weight of acrylic acid having an intrinsic viscosity of 1.9 dl/g polymerised in acetone according to the method given in United Kingdom Application No. 8106707.

The embossed film was then removed from the composite strip and the strip cut into suitable sized dressings of the invention.

Example 24

Wound dressings were prepared in the same manner as Example 22 using a cast polybutadiene (Ref RB 830) net (6 apertures/cm) instead of a polyurethane net.

Adherency Testing

A group of 9 guinea pigs were clipped and depilated over the thorax/abdominal region. Two partial thickness burns, 2.5 cm in diameter were created, one on each flank, by contact with hot water at 65° C. for 15 seconds. The skin was dried and the burnt area scraped with a scalpel blade to remove the epidermis. Histological sections have previously shown that this technique separates the skin between the epidermis and dermis. Dressings were applied to the wound with a margin of approximately 1 cm all round. Crepe bandage was wrapped round the animal and secured with an elastic adhesive bandage. The dressings were left in place for 24 hours. The animals were then sacrificed with an intracardiac injection of pentobarbitone and full thickness sections of skin with a generous margin around the wound was taken from the animal. The dressings were then peeled from the skin biopsy using an Instron tensile testing machine at a peel speed of 5 inches per minute. The mean, maximum and integrated total force of removal (g) were recorded. The product of Example 1 required 210 g for removal.

The energy for removal (milli-joules) of the dressing from the skin biopsy can be calculated from the peel adhesion results. The dressings of Examples 3 and 22 had an energy removal which was approximately half that of a Melolin* dressing (energy of removal approximately 6.5 mJ/cm$^2$).

*Melolin is an absorbent wound dressing consisting of a perforated polyester wound facing film adhered to an absorbent pad of lightly bonded cotton and rayon fibre mixture (made by T. J. Smith and Nephew Limited).

What is claimed is:

1. A conformable low adherency wound dressing which comprises
   (a) a low adherency wound facing layer 0.05 to 2.5 mm thick which is a conformable elastomeric apertured net;
   (b) an absorbent layer comprising a conformable hydrophilic foam 0.5 to 20 mm thick; and
   (c) a continuous conformable moisture vapour permeable outer film layer which acts as a bacterial barrier and has a moisture vapour transmission rate of from 300 to 5000 grams/square meter/24 hours at 37° C. at 100% to 10% relative humidity difference, said wound facing layer and said outer layer being laminated to opposing faces of said absorbent layer over the operative area of the dressing.

2. A dressing according to claim 1, in which the conformable elastomeric net comprises an integral net.

3. A dressing according to claim 1, in which the conformable elastomeric net has 4 to 40 apertures per cm.

4. A dressing according to claim 1, in which the conformable elastomeric net comprises a polyurethane.

5. A dressing according to claim 1, in which the continuous conformable layer has a moisture vapour transmission rate of 500 to 2000 grams/square meter/24 hours at 37° C. at 100% to 10% relative humidity difference.

6. A dressing according to claim 1, in which the continuous moisture vapour transmitting conformable film layer comprises a polyurethane.

7. A dressing according to claim 1, in which the conformable outer film layer comprises a moisture vapour transmitting adhesive layer.

8. A dressing according to claim 1, in which the conformable hydrophilic foam is a foam of hydrophilic polymer.

9. A dressing according to claim 8, in which the hydrophilic polymer is hydrophilic polyurethane.

10. A dressing according to claim 1, in which the hydrophilic foam comprises an open cell foam with a cell size of 50 to 500 microns.

11. A dressing according to claim 1, in which the hydrophilic foam comprises an open cell foam in which 30% to 60% of the total area of the cells are membrane openings.

12. A sterile dressing according to claim 1, within a bacteria impervious package.

* * * * *